(12) United States Patent
Minami

(10) Patent No.: US 6,319,196 B1
(45) Date of Patent: Nov. 20, 2001

(54) IMAGING ELEMENT ASSEMBLY UNIT FOR ENDOSCOPE

(75) Inventor: Itsuji Minami, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/340,051

(22) Filed: Jun. 28, 1999

(30) Foreign Application Priority Data

Jul. 6, 1998 (JP) .................................................. 10-190226

(51) Int. Cl.[7] .................................................. A61B 1/05
(52) U.S. Cl. ........................... 600/130; 600/109; 348/76
(58) Field of Search .......................... 600/109–112, 129, 600/130; 348/76

(56) References Cited

U.S. PATENT DOCUMENTS 5,754,313 * 5/1998 Pelchy et al. ........................ 358/473
6,071,760 * 6/2000 Nakada ................................ 438/123

FOREIGN PATENT DOCUMENTS

10216083 A   8/1998 (JP) .
05015489 A   1/1993 (JP) .................................. A61B/1/04

* cited by examiner

*Primary Examiner*—John Mulcahy
(74) *Attorney, Agent, or Firm*—Ronald R. Snider; Snider & Associates

(57) ABSTRACT

The present invention is an imaging element assembly unit in which it can easily be promoted to make the diameter of the tip portion of an endoscope thinner by changing the configuration of a circuit board in relation to an image element. In this assembly unit, an imaging element body formed while holding a lead portion between an electrode of a CCD and a cover glass is produced, for example, on the TAB system, and this imaging element body is connected to a circuit board having a storing groove. Then, the width in the electrode arranging direction of this circuit board is formed shorter than the width in the electrode arranging direction of the CCD, and at a position where both ends of this circuit board retreat from both ends of the CCD, these are connected by a lead portion. By doing so, the diameter of the tip portion can be made thinner since the sides of both ends of the circuit board arranged on the side of the inside peripheral surface of a tip portion holding barrel retreat inside.

5 Claims, 4 Drawing Sheets

US 6,319,196 B1

IMAGING ELEMENT ASSEMBLY UNIT FOR ENDOSCOPE

BACKGROUND OF THE INVENTION

This application claims the priority of Japanese Patent Application No. 10-190226 filed on Jul. 6, 1998 which is incorporated herein by reference.

1. Field of the Invention

The present invention relates to an imaging element assembly unit for an endoscope, and more particularly, it relates to an assembly structure of an imaging element in which it is possible to make the diameter of the tip portion where the imaging element is arranged thinner.

2. Description of the Prior Art

In FIG. 8, one example (Japanese Patent Application Laid-Open Publication No. 5-15489) of the configuration of a conventional imaging element assembly body to try to make the diameter of the tip portion of an electronic endoscope thinner is shown. In FIG. 8, a package 2 to which a CCD 1 as a solid imaging element is connected and which also does the job of a circuit board has a side portion thereof cut off to be in an open state. To this package 2, a CCD 1 is connected by a bonding wire 3, and after that, a cover glass 4 is adhered onto the upper surface of the package by adhesives or the like, and further, similar adhesives or the like are also filled up in the side portion, and the interior of this package 2 is kept in an airtight state.

According to the configuration like this, the side portion of a conventionally used complete box-like package is cut off, and therefore the width of the imaging element assembly body can be made smaller, and it is possible to make the diameter of the tip portion thinner by arranging the longitudinal direction of this package 2, for example, along an endoscope axis 100. Furthermore, in the package 2, the interior has an airtight structure, and therefore, the degradation of a color filter formed on the imaging surface of the CCD 1 can be restrained, and in the meantime, the protection of a micro lens arranged on this color filter or the like becomes possible.

However, in the configuration using the above package 2, it is difficult to further make the diameter thinner, and if it is possible to further make the diameter thinner by suitably changing the structure of an imaging element or a circuit board at the imaging element assembly part like this, an assembly unit with a high use value can be obtained.

The present invention is made due to the above problems, and it is an object thereof to provide an imaging element assembly body for an endoscope in which it can easily be promoted to make the diameter of the tip portion of an endoscope thinner by changing the configuration of a circuit board in relation to an imaging element.

BRIEF SUMMARY OF THE INVENTION

In order to attain the object, an imaging element assembly unit for an endoscope according to the present invention, comprises an imaging element which images the interior of an observed object, and a circuit board including an electrode (terminal) to which an electrode of this imaging element is connected by a lead wire and formed so that the width in the electrode arranging direction thereof may be shorter than the width in the electrode arranging direction of the imaging element, wherein these are connected by the lead wire at a position where both ends of the circuit board retreat inside from both ends of the imaging element in each of the electrode arranging directions.

Furthermore, by sticking a cover glass on the imaging surface side of the imaging element while holding the lead wire in between, an airtight space can be formed on this imaging surface at given intervals.

According to the above configuration, a form where both sides in the electrode arranging direction of the circuit board retreat inside from both sides of the imaging element is made, and for example, when considering the case where both sides of these circuit board and imaging element are positioned near the inside peripheral surface of a round holding barrel which is an armor body, the inside diameter of the holding barrel can be made smaller by the size corresponding to the retreat of both sides of the narrowed circuit board to the inside, and it is possible to make the diameter thinner by this.

BRIEF DESCRIPTION OF THE DRAWINGS

FIG. 3 (B) is a side view of a circuit board of the first example;

DETAILED DESCRIPTION OF THE PREFERRED EMBODIMENTS

Figure 1A:
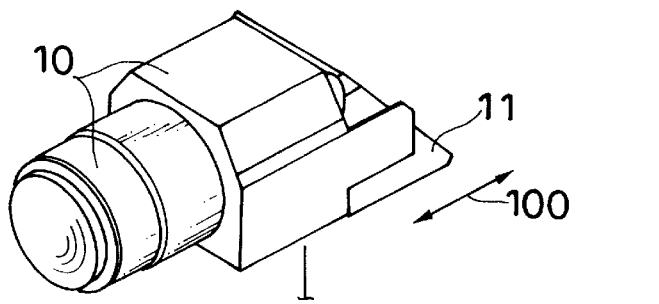
FIGS. 1(A) to 1(C) are exploded perspective illustrations showing the configuration of an imaging element assembly unit for an endoscope according to a first example of the embodiment of the present invention.

In FIG. 1 to FIG. 5, the configuration of an imaging element assembly body for an endoscope according to a first example of the embodiment is shown, and this first example is an example of a type of placing an imaging element horizontally (type of placing an imaging element in parallel with an endoscope axis 100). In FIGS. 1(A) to 1(C), an objective lens system 10 is arranged along the endoscope axis (longitudinal axis) 100, and to the rear end surface of this objective lens system 10, a rectangular prism 11 is attached. Then, to the under side of this prism 11, an imaging element body 12 is optically connected, and this imaging element body (unit) 12 is connected to a circuit board 13.

In this example, the imaging element body 12 is produced, for example, on the TAB (Tape Automated Bonding) system. This TAB system (described in detail in Japanese Patent Application No. 9-39936) is a mass production system in which a conductive lead portion (inner lead and outer lead) and a cover glass are packaged to an imaging surface of an imaging element assembled in a carrier tape to be carried, and the production, inspection, or the like can be performed like a flow production system.

Figure 1B:
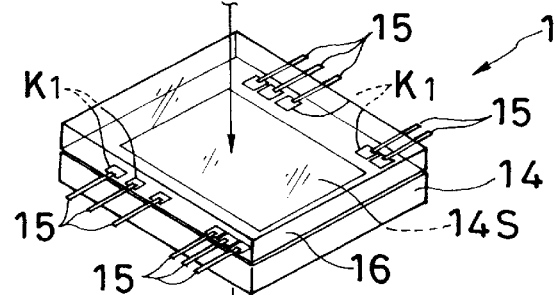
Figure 1C:
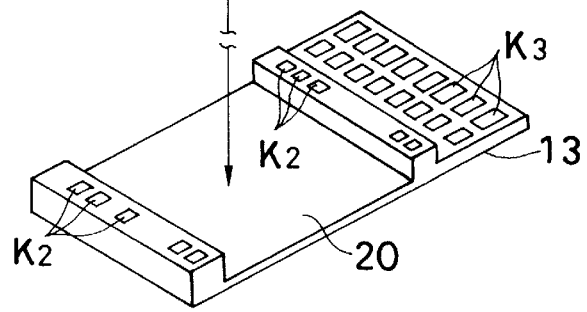
Figure 2:
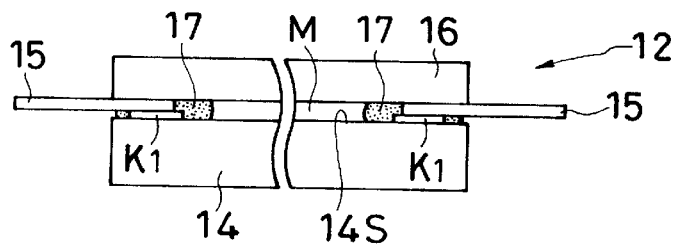
FIG. 2 is an enlarged side view showing the configuration of an imaging element body used in the example of the embodiment.

That is, as shown in an enlarged view of FIG. 2, to an electrode K1 arranged on the imaging surface 14S side of a CCD 14 which is a solid imaging element, a flat-bar-like lead (inner lead) portion (wire) 15 is connected, and a cover glass 16 [cover glass in FIG. 1(B) or the like is shown in the state of a perspective view] is adhered by adhesives 17 or the like poured on the imaging surface 14S side around the periphery thereof so as to hold this lead portion 15 in between. Consequently, the imaging element body 12 in which an airtight space M with a little spacing is formed on the upper side of the imaging surface 14S, and in the case of being produced on this TAB system, an imaging element body 12 of this example can be easily obtained by performing the cutting from the carrier tape at the part of the inner lead.

Figure 3A:
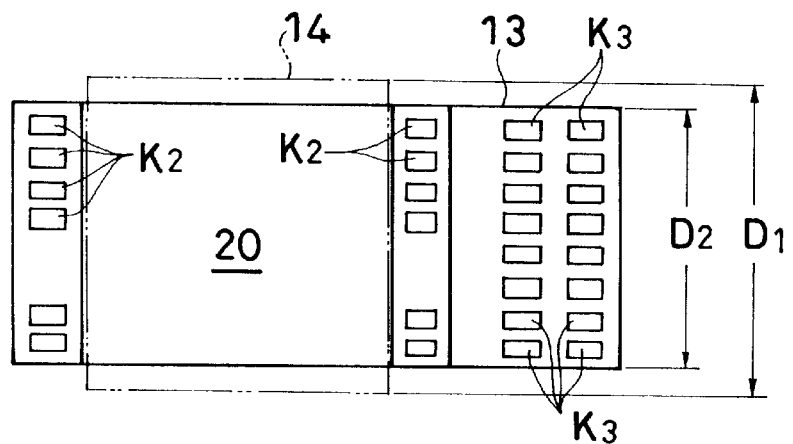
FIG. 3 (A) is a plan view showing the configuration of a circuit board used in the first example, and FIG. 3 (B) is a side view.
Figure 3B:
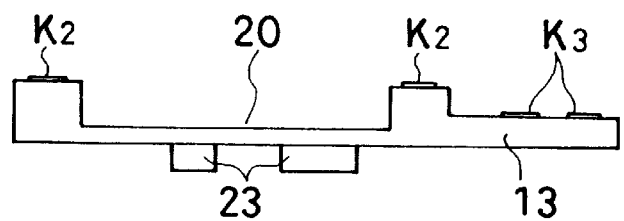

In FIG. 3, the details of a circuit board 13 to which the imaging element body 12 is attached are shown, and this circuit board 13 has a storing groove 20 with a depth approximately equal to the height of the CCD 14, and to a rising edge portion of this storing groove 20, an electrode K2 for connecting the lead portion 15 is formed. This electrode K2 is wired and connected to an electrode K3 formed at the rear end portion of the circuit board 13 through a through hole or the like (wiring is also formed at the bottom surface portion of the storing portion 20), and to this electrode K3, a signal wire 21 (FIG. 4) for transmitting a video signal or the like is connected.

Then, the width D2 in the arranging direction of the electrodes K2 of this circuit board 13 is made shorter than the width D1 in the arranging direction of the electrodes K1 of the CCD 14, and as shown in FIG. 3, both members 13, 14 are connected and arranged in the state where the sides of both ends of the circuit board 13 in this electrode arranging direction retreat inside from the sides in the same direction of the CCD 14. By the way, to this circuit board 13, a necessary circuit member 23 is attached at a suitable position.

Figure 4:
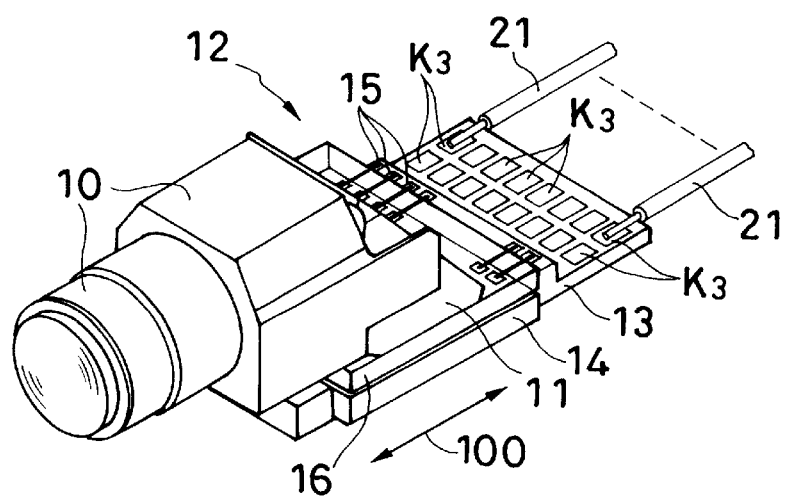
FIG. 4 is a perspective view showing a state where an imaging element assembly unit of the first example is assembled.

According to the configuration of the first example like this, as shown in FIG. 1, the lead portion 15 of the imaging element body 12 is connected to the electrode K2 of the circuit board 13, and on the cover glass 16 of this imaging element body 12, the prism 11 arranged at the rear end portion of the objective lens system member 10 is optically connected. By doing so, the assembly body in the state of FIG. 4 is formed, and to the electrode K3 at the rear end portion of this circuit board 13, the signal wire 21 is connected.

Figure 5:
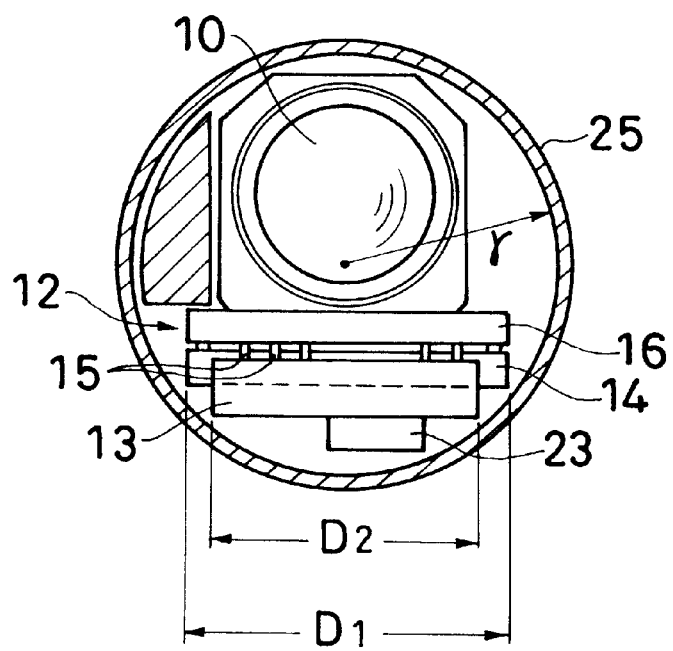
FIG. 5 is a figure of the interior in a state where the imaging element assembly unit of the first example is arranged at the tip portion (arrangement considering no other member) when seen from the front.

In FIG. 5, a state where the imaging element body 12 of the first example is arranged in a tip portion holding barrel, and here, other members such as a light guide or a dealing tool through channel are not considered. It is understood from FIG. 5 that when considering a case where the under surface of the circuit board 13 approaches the inside peripheral surface of the tip portion holding barrel 25, the width D2 in the electrode arranging direction of this circuit board 13 is shorter than the width D1 in the same direction of the CCD 14, and therefore, the radius r of the holding barrel 25 can be made smaller even if it is compared with that in the case where these widths D1, D2 are the same. Consequently, it is possible to make the diameter of the tip portion of an endoscope thinner, and this can be said similarly even in the case where the circuit board 13 is not arranged near the inside peripheral surface of the holding barrel 25. For example, in the case where another member is arranged between both end portions of the circuit board 13 and the holding barrel 25, this other member can be brought closer to the center side, and as a result, the radius r of the holding barrel 25 becomes smaller.

Figure 6:
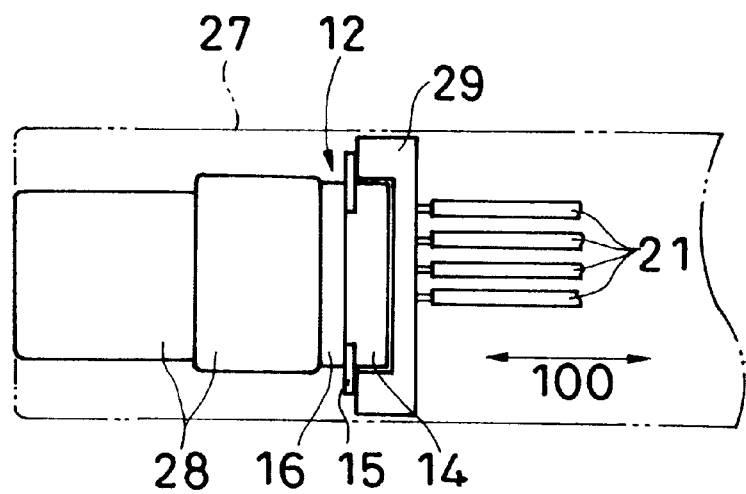
FIG. 6 is a side view showing the configuration of an imaging element assembly unit of a second example.
Figure 7:
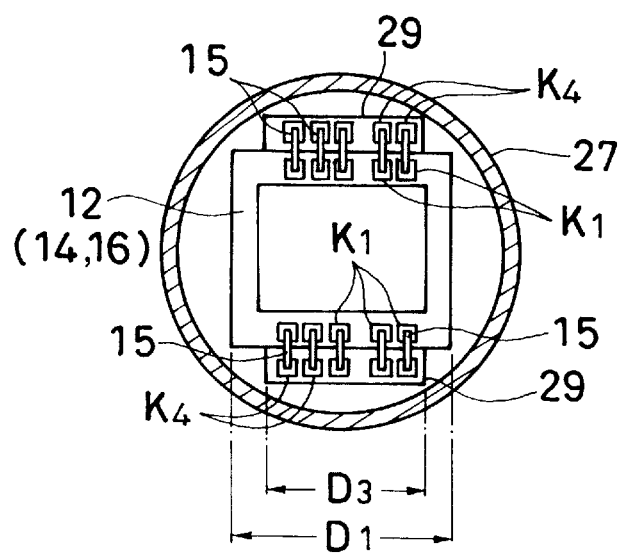
FIG. 7 is a figure of the interior in a state where an imaging element assembly unit of the second example is arranged at the tip portion when seen from the front.
Figure 8:
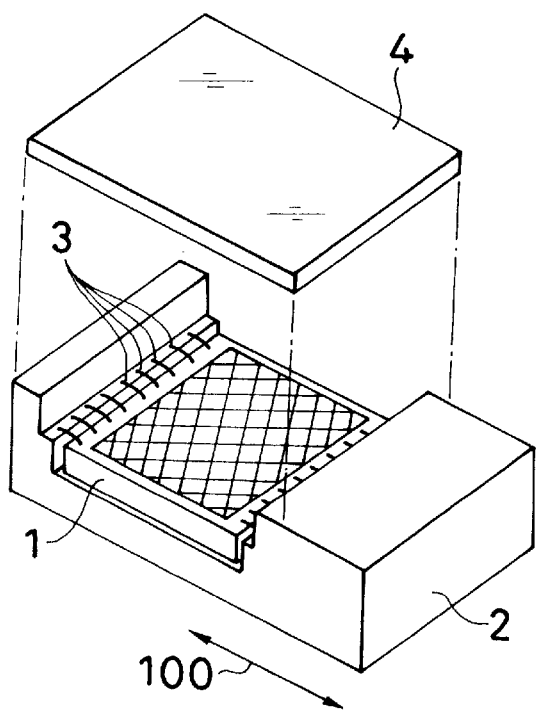
FIG. 8 is a perspective view showing the configuration of a conventional imaging element assembly body for an endoscope.

In FIG. 6 and FIG. 7, the configuration of a second example of the embodiment is shown, and this second example is an example of a type of placing an imaging element perpendicularly (perpendicular to the endoscope axis 100). As shown in FIG. 6, an objective lens system 28 is arranged along the endoscope axis 100 in the tip portion holding barrel 27, and to the rear end surface of this objective lens system 28, an imaging element body 12 similar to that of the first example is optically connected in the state of being perpendicular to the endoscope axis 100.

The configuration of this imaging element body 12 is similar to that described in FIG. 2, and this imaging element body 12 is connected to a circuit board 29 for a type of placing an imaging element perpendicularly. That is, as shown in FIG. 7, on the circuit board 29, a plurality of electrodes K4 for connecting the lead portions 15 are arranged, and this electrode is wired to an electrode (not shown in the figure) provided on the rear surface. To this electrode on the rear surface of the circuit board 29, a signal wire 21 is connected as shown in FIG. 6.

Then, in this second example, the width D3 in the arranging direction of the electrodes K4 of the circuit board 29 is also made shorter than the width D1 in the arranging direction of the electrodes K1 of the CCD 14, and both are connected by the lead portion 15 in the state where the sides of both ends in the electrode arranging direction of this circuit board 29 retreat inside from the sides in the same direction of the CCD 14.

In the configuration of the second example like this, as shown in FIG. 7, the width D3 in the electrode arranging direction of this circuit board 29 is also shorter than the width D1 of the CCD 14, and therefore, the radius of the holding barrel 27 can be made smaller when compared with that in the case where these widths D1, D3 are the same, and consequently, it is possible to make the diameter of the tip portion of an endoscope thinner.

In the examples of the embodiment, examples in which an airtight space M is set on the imaging surface 14S of the CCD 14 were described, but a configuration of arranging no airtight space on the imaging surface is also used, and in this case, the present invention can also be applied.

As mentioned above, according to the present invention, it is possible to reduce the diameter of the tip portion holding barrel corresponding to the quantity of the retreat of both ends of the circuit board to the inside, and there is such an advantage that it can be promoted to make the diameter of the tip portion of an endoscope thinner by a simple composition. Furthermore, since a cover glass is stuck to the imaging element by adhesives while holding lead portions in between and an airtight space with a given spacing is formed on the imaging surface, it is possible to obtain an assembly unit of an imaging element in which it is necessary to adopt air tightness at low cost.

What is claimed is:

1. An imaging element assembly unit for an endoscope, comprising:

an imaging element for imaging an interior of an observed object;

a circuit board including electrodes to which electrodes of the imaging element are connected by lead wires, and formed so that width in a circuit board electrode arranging direction therefore is shorter than width in an electrode arranging direction of said imaging element, wherein said imaging element is disposed on said circuit board wherein an imaging surface of said imaging element is approximately parallel to an electrode arranging surface of said circuit board, and the circuit board electrodes are connected by said lead wires at a position where both ends of said circuit board retreat inside from both ends of said imaging element in the electrode arranging direction of said imaging element.

2. The imaging element assembly unit for an endoscope according to claim 1, wherein an airtight space with a given spacing is formed on an imaging surface by sticking a cover glass while holding said lead wire between the imaging surface side of said imaging element and the cover glass.

3. An imaging element assembly unit for an endoscope, comprising:

an imaging element for imaging an interior of an observed object;

a circuit board including electrodes to which electrodes of the imaging element are connected by lead wires, and wherein the circuit board is formed so that width in a circuit board electrode arranging direction is shorter than width in an electrode arranging direction of said imaging element, wherein the circuit board electrodes are connected by said lead wires at a position where both ends of said circuit board retreat inside from both ends of said imaging element in the electrode arranging direction of said imaging element;

wherein said circuit board has a storing groove for holding said imaging element and the circuit board electrode for connecting the lead portion is formed to a rising edge portion of said storing groove.

4. An imaging element assembly unit for an endoscope, comprising:

an imaging element for imaging an interior of an observed object;

a circuit board including electrodes to which electrodes of the imaging element are connected by lead wires, and formed so that circuit board width in a circuit board electrode arranging direction therefore is shorter than width in an electrode arranging direction of said imaging element, and both sides of said circuit board are positioned near the inside peripheral surface of a round holding barrel which is an armor body, and wherein said imaging element is disposed on said circuit board wherein an imaging surface of said imaging element is approximately parallel to an electrode arranging surface of said circuit board, and the circuit board electrodes are connected by said lead wires at a position where both ends of said circuit board retreat inside from both ends of said imaging element in the electrode arranging direction of said imaging element.

5. The imaging element assembly unit for an endoscope according to claim 3, wherein said storing grove is approximately equal to a height of the imaging element.

* * * * *

UNITED STATES PATENT AND TRADEMARK OFFICE
CERTIFICATE OF CORRECTION

PATENT NO. : 6,319,196 B1
DATED : November 20, 2001
INVENTOR(S) : Itsuji Minami

Page 1 of 1

It is certified that error appears in the above-identified patent and that said Letters Patent is hereby corrected as shown below:

Column 6,
Line 29, delete "grove" and substitute therefore -- groove --.

Signed and Sealed this

Ninth Day of April, 2002

Attest:

JAMES E. ROGAN
Attesting Officer  Director of the United States Patent and Trademark Office